United States Patent
Oga

(10) Patent No.: US 11,391,731 B2
(45) Date of Patent: Jul. 19, 2022

(54) TARGET SUBSTANCE DETECTION METHOD, TARGET SUBSTANCE DETECTION KIT, AND TARGET SUBSTANCE DETECTION SYSTEM

(71) Applicant: ARKRAY, Inc., Kyoto (JP)

(72) Inventor: Misaki Oga, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 16/905,460

(22) Filed: Jun. 18, 2020

(65) Prior Publication Data
US 2020/0400658 A1  Dec. 24, 2020

(30) Foreign Application Priority Data
Jun. 19, 2019  (JP) .............. JP2019-114031

(51) Int. Cl.
  *G01N 33/543*  (2006.01)
  *G01N 33/569*  (2006.01)
  *C12N 15/115*  (2010.01)

(52) U.S. Cl.
  CPC ..... *G01N 33/54306* (2013.01); *C12N 15/115* (2013.01); *G01N 33/54393* (2013.01); *G01N 33/56983* (2013.01); *C12N 2310/16* (2013.01); *C12N 2310/3517* (2013.01); *C12N 2310/3519* (2013.01); *G01N 2333/11* (2013.01)

(58) Field of Classification Search
  None
  See application file for complete search history.

(56) References Cited

U.S. PATENT DOCUMENTS

| | | |
|---|---|---|
| 5,641,629 A | 6/1997 | Pitner et al. |
| 5,824,478 A | 10/1998 | Muller |
| 2002/0037506 A1* | 3/2002 | Lin ............ G01N 33/86 435/6.11 |
| 2008/0299558 A1 | 12/2008 | Kondo et al. |
| 2012/0220051 A1 | 8/2012 | Yin et al. |

FOREIGN PATENT DOCUMENTS

| | | |
|---|---|---|
| JP | H10-048216 A | 2/1998 |
| JP | H10-512751 A | 12/1998 |
| JP | 2012-533064 A | 12/2012 |
| WO | 96/22383 A1 | 7/1996 |
| WO | 2011/005357 A2 | 1/2011 |

OTHER PUBLICATIONS

Huang et al. Anal. Chem. 2013, vol. 85, pp. 10842-10849.*
Zhou et al. Nucleic Acids Research 2009, vol. 37, pp. 3094-3109.*
John G. Bruno; "Application of DNA Aptamers and Quantum Dots to Lateral Flow Test Strips for Detection of Foodborne Pathogens with Improved Sensitivity versus Colloidal Gold"; Pathogens; Jun. 2014; pp. 341-355; vol. 3.
The extended European search report issued by the European Patent Office dated Oct. 21, 2020, which corresponds to European Patent Application No. 20181054.6-1118 and is related to U.S. Appl. No. 16/905,460.

* cited by examiner

Primary Examiner — Tracy Vivlemore
(74) Attorney, Agent, or Firm — Studebaker & Brackett PC

(57) ABSTRACT

The present disclosure provides, in one aspect, a target substance detection method in which a trapping substance that indirectly binds to both an immobilization side (support side) and a detection side (reporter side), which is a method for detecting a target substance in a sample. The method includes a reaction step of reacting the sample, a support including a first binding portion, a reporter substance including a second binding portion, a first trapping substance that includes a first binding partner portion capable of binding to the first binding portion and that can bind to the target substance, and a second trapping substance that includes a second binding partner portion capable of binding to the second binding portion and that can bind to the target substance; and a detection step of detecting a signal from the reporter substance.

10 Claims, 3 Drawing Sheets
Specification includes a Sequence Listing.

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Bindng part

<400> SEQUENCE: 1 ttttttttttt tttttttttt tttt                                             24

<210> SEQ ID NO 2
<211> LENGTH: 99
<212> TYPE: RNA
<213> ORGANISM: Artificial Sequence
<220> FEATURE:
<223> OTHER INFORMATION: Nucleic acid aptamer probe 1.

<400> SEQUENCE: 2
gggagaauuc cgaccagaag aauaguagaa ugagcucugu cggacccagc cuuuccucuc        60
uccuuccucu ucuuuaaaaa aaaaaaaaaa aaaaaaaa                                99

<210> SEQ ID NO 3
<211> LENGTH: 61
<212> TYPE: RNA
<213> ORGANISM: Artificial Sequence
<220> FEATURE:
<223> OTHER INFORMATION: Nucleic acid aptamer probe 2.

<400> SEQUENCE: 3 gggguuagcag ucggcaugcg guacagacag acccuuuaaa aaaaaaaaaa aaaaaaaaa        60 a                                                                        61

TARGET SUBSTANCE DETECTION METHOD, TARGET SUBSTANCE DETECTION KIT, AND TARGET SUBSTANCE DETECTION SYSTEM

CROSS-REFERENCE TO RELATED APPLICATION

This application claims benefit of priority to Japanese Patent Application No. JP2019-114031, filed Jun. 19, 2019, the entire content of which is incorporated herein by reference.

REFERENCE TO AN ELECTRONIC SEQUENCE LISTING

The contents of the electronic sequence listing (sequence_listing.txt; Date of Creation: Jun. 17, 2020; and Size: 988 bytes) is herein incorporated by reference in its entirety.

BACKGROUND

1. Field

The present disclosure relates to a target substance detection method, a target substance detection kit and a target substance detection system in which trapping substances are used.

2. Description of Related Art

An immuno chromatographic method, an ELISA method, a flow-through method, a surface plasmon resonance (SPR) method, a beads assay method, and the like are known as methods for detecting a target substance. For example, in an immuno chromatographic detection method, a protein such as an antigen or an antibody is used to trap a detection-target substance (target substance) in a sample (JP 2012-533064A). For the purpose of enhancing sensitivity, the development of an immuno chromatographic detection method in which nucleic-acid aptamers are used has been started (JP H10-512751A).

As a method for immobilizing a nucleic-acid aptamer, an end of a nucleic-acid aptamer that specifically binds to a detection-target substance is modified with $NH_2$, biotin, digoxigenin, or the like, and the nucleic-acid aptamer is immobilized on a nitrocellulose membrane or coupled to a detecting substance via the modified end (Bruno, Pathogens. 2014 June; 3(2): 341-355). A UV irradiation method is employed to directly couple a nucleic-acid aptamer to an immobilization carrier. Streptavidin is employed for indirect coupling of a biotin-modified aptamer. An anti-digoxigenin antibody is employed for a digoxigenin-modified aptamer. In order to indirectly couple a nucleic-acid aptamer to an immobilization carrier without using a protein, a method can also be used in which single-stranded DNA or single-stranded RNA having a sequence complementary to the nucleic-acid aptamer is coupled to an immobilization carrier, and the nucleic-acid aptamer is coupled to the immobilization carrier through complementary coupling (JP H10-48216A).

SUMMARY

In a conventional method for detecting a target substance (the so-called sandwich method), a trapping substance is directly immobilized on at least one of the immobilization side (the support substance side) and the detection side (the reporter side) before a sample containing a target substance is brought into contact therewith. Accordingly, when the target substance is changed to another one, it is necessary to change the immobilized trapping substance to a trapping substance corresponding to the new target substance. In order to make this change, it is necessary to redesign the trapping substance together with the support and/or the reporter substance on which the trapping substance is immobilized, and thus the immobilization of the trapping substance needs to be examined again.

However, in the conventional detection method in which a trapping substance is directly immobilized, when a chemical reaction or the like for immobilizing the trapping substance is performed, the trapping substance itself is also exposed to the reaction. This causes a problem in that the ability of the trapping substance to recognize a target substance is lost or impaired, for example. Accordingly, it is necessary to examine the immobilization reaction conditions and search for the optimum conditions. A lot of samples are required for the examination of the conditions, and time for the examination is required. Furthermore, in the early stages of a search for a trapping substance, there is a problem in that the conditions need to be examined regarding many candidate trapping substances, and it takes a lot of time.

Examples of a method for immobilizing a nucleic-acid aptamer on a carrier include immobilization methods in which chemical formation of a covalent bond, formation of a covalent bond with physical energy caused by UV irradiation, and the like are utilized (JP H10-48216A). However, these immobilization processes cause damage to the nucleic-acid aptamer itself, which causes impairment of the ability of the nucleic-acid aptamer to bind to a target substance, or loss of the functions of the nucleic-acid aptamer.

To address this, an aspect of the present disclosure provides a target substance detection method in which an immobilization side (support substance side) and a trapping substance can be indirectly coupled to each other and a detection side (reporter side) and the trapping substance can be indirectly coupled to each other.

Regarding a conventional immuno chromatographic method, when a sandwich method in which a target substance is trapped using two types of binding substances (e.g., antibodies or haptens) is performed, the two types of binding substances are designed such that one specifically binds to the immobilization side (support side) and the other specifically binds to the detection side (reporter substance side). For example, regarding a sandwich method in which a target substance is trapped using two different types of monoclonal antibodies, it is known that, according to the types of antibodies, some are preferably used on the immobilization side (support side) and others are preferably used on the detection side (reporter substance side).

One example of the detection target of the immuno chromatography is an influenza virus. In order to identify subtypes and drug-resistant strains of an influenza virus, trapping substances such as antibodies and nucleic-acid aptamers targeting hemagglutinin (HA), neuraminidases, and RNA polymerases are needed in addition to those targeting nucleoproteins. However, these virus proteins are likely to undergo mutation, and the change of the trapping substance is imperative to maintain the sensitivity. This is not limited to the influenza virus and also applies to viruses, bacteria, fungi, and the like that may undergo mutation.

When an aptamer is applied to immuno chromatography, or an aptamer obtained for a new target substance or a mutated target substance is applied to immuno chromatography, it is necessary to design two types of aptamer probes, namely aptamer probes for the immobilization side (support side) and the detection side (reporter substance side), relative to one type of aptamer in the conventional method.

If one of the two types of aptamer probes that bind to a target is limited to being coupled to the immobilization side (support side) and the other is limited to being coupled to the detection side (reporter substance side), it is conceivable that the reaction efficiency of binding to the support and the reporter (target substance trapping efficiency) will decrease.

Accordingly, another aspect of the present disclosure provides an immuno chromatographic detection method in which an aptamer probe that can indirectly bind to both the immobilization side (support side) and the detection side (reporter substance side) is used.

An aspect of the present disclosure relates to a method for detecting a target substance in a sample, and the method includes: a reaction step of reacting the sample, a support including a first binding portion, a reporter substance including a second binding portion, a first trapping substance that includes a first binding partner portion capable of binding to the first binding portion and the second binding portion and that can bind to the target substance, and a second trapping substance that includes a second binding partner portion capable of binding to the first binding portion and the second binding portion and that can bind to the target substance to form a complex of "support—first trapping substance—target substance—second trapping substance—reporter substance" or a complex of "support—second trapping substance—target substance—first trapping substance—reporter substance"; and a detection step of detecting a signal from the reporter substance in the complex. This method is also referred to as a "first detection method according to the present disclosure" hereinafter.

Another aspect of the present disclosure relates to a target substance detection system for performing the above-mentioned method for detecting a target substance in a sample. This system is also referred to as a "first detection system according to the present disclosure" hereinafter.

Another aspect of the present disclosure relates to a method for detecting a target substance in a sample using an immuno chromatographic method, and the method includes: using an aptamer probe including an aptamer portion that can bind to the target substance, and a binding partner portion that can bind to both a binding portion immobilized on (and forming part of) a support and a binding portion immobilized on (and forming part of) a reporter substance to trap the target substance and the reporter substance on the support in a binding state represented as "support—aptamer probe—target substance—aptamer probe—reporter substance"; and detecting a signal from the reporter substance. The above method uses one or more aptamer probe. This method is also referred to as a "second detection method according to the present disclosure" hereinafter.

Another aspect of the present disclosure relates to a target substance detection system in which an immuno chromatographic method is used, and the system includes:
an immuno chromatographic test piece including a detection region on which a binding portion is immobilized;
a reporter substance on which a binding portion is immobilized; and
an aptamer probe including a binding partner portion that can bind to both the binding portion of the detection region and the binding portion of the reporter substance, and an aptamer portion that can bind to the target substance. This system is also referred to as a "second detection system according to the present disclosure" hereinafter.

Another aspect of the present disclosure relates to a kit for performing the second detection method according to the present disclosure, and the kit includes:
an immuno chromatographic test piece including a detection region on which a binding portion is immobilized;
a reporter substance on which a binding portion is immobilized; and
an aptamer probe including a binding partner portion that can bind to both the binding portion of the detection region and the binding portion of the reporter substance, and an aptamer portion that can bind to the target substance. This kit is also referred to as a "second detection kit according to the present disclosure" hereinafter.

With the first aspect according to the present disclosure (including the first detection method and the first detection system according to the present disclosure), a target substance detection method in which a trapping substance that can indirectly bind to both the immobilization side (support side) and the detection side (reporter substance side) is used can be provided, for example.

As a result, even if there are many candidate trapping substances, defining the first binding portion and the second binding portion in advance makes it possible to perform an assay in which many candidate trapping substances are utilized as they are without examining the conditions for immobilizing the candidate trapping substances. This leads to a reduction in the amounts of examination samples and thus a significant reduction in the examination time. In particular, when many trapping substances are subjected to screening in a trapping substance selecting step of the SELEX method or the like, employing the present disclosure makes it possible to significantly reduce the screening time and reduce the cost.

Moreover, since processing for immobilizing the trapping substances on a support or a reporter substance is not performed, damage to the trapping substance due to the immobilization processing can be minimized, thus making it possible to perform an assay while maintaining the function of recognizing a target substance.

Furthermore, immobilizing the trapping substance via the first binding portion on the immobilization side makes it possible to maintain the orientation of the trapping substance. Thus, for example, the trapping efficiency of the target substance by the trapping substance can be improved. The immobilization of the trapping substance via the first binding portion on the immobilization side can be performed, for example, by providing a binding partner portion at a position of the trapping substance that is different from the target substance recognition portion (portion that binds the target substance) and binding the binding partner portion to the first binding portion on the immobilization side. Thus, the trapping substance can be indirectly immobilized on the immobilization side. Thus, since the target substance recognition portion of the trapping substance is not used for binding to the support, the trapping substance is immobilized on the support in a state in which the trapping substance can bind to the target substance (that is, a state in which the target substance recognition portion of the trapping substance is exposed and the orientation of trapping substance is retained).

With the second aspect according to the present disclosure (including the second detection method, the second detection system, and the second detection kit according to the present disclosure), an immuno chromatographic detection method in which an aptamer probe that can bind to both the immobilization side (support side) and the detection side (reporter substance side) is used can be performed.

In one or more embodiments that are not limited, when a plurality of aptamers can bind to a target substance, preparing a single type of aptamer makes it possible to perform the immuno chromatographic detection method.

DETAILED DESCRIPTION

First Aspect

Figure 1:
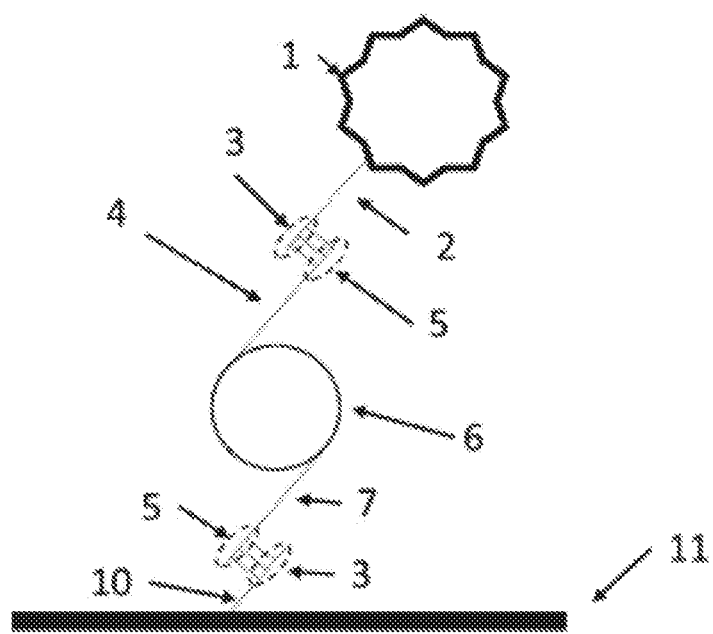
FIG. 1 is a schematic view of an embodiment of the first aspect or the second aspect, illustrating a state in which a reporter substance 1 and a target substance 6 are trapped on a support 11 via two types of aptamer probes 4 and 7 (a first trapping substance and a second trapping substance). The aptamer probes 4 and 7 include different aptamer portions and a common binding partner portion 5, and the binding partner portion 5 can bind to both a binding portion 3 of a binding portion probe 2 immobilized on (and forming part of) the reporter substance 1 and a binding portion 3 of a binding portion probe 10 immobilized on (and forming part of) the support 11. At this time, the binding portion 3 and the binding partner portion 5 indirectly (i.e. non-covalently) bind to each other, and the aptamer probes 4 and 7 are indirectly immobilized on the reporter substance 1 or the support 11.

The first aspect according to the present disclosure is based on the fact that a target substance detecting method in which trapping substances are used has a problem in that, in the case where the trapping substances are directly coupled to a support or a reporter substance, when the target substance is changed to another one, it is not sufficient that only the trapping substance is redesigned and it is necessary to redesign the trapping substance together with the support and the reporter substance on which the trapping substance is immobilized, which leads to an increase in cost and time, for example. A solution to such a problem was found in which, even when a new trapping substance based on the change of the target substance is used, defining binding modules (for example, a binding portion and a binding partner portion) for immobilizing the trapping substance on the support and the reporter substance in advance makes it possible to utilize the new trapping substance as it is without examining the conditions for immobilizing the trapping substance on the support and the reporter substance.

With the first aspect, in one or more embodiments, a trapping substance is indirectly immobilized on the support or the reporter substance via a certain binding module, and therefore, even when a target substance is changed, the target substance detection method can be changed so as to be suitable for a newly targeted target substance by changing only a first trapping substance including a first binding partner portion and a second trapping substance including a second binding partner portion without changing the support including the first binding portion and the reporter substance including the second binding portion, thus making it possible to provide a target substance detecting method that can be set up and performed at a low cost for a short period of time.

First Detection Method

The first detection method according to the present disclosure is a method for detecting a target substance in a sample, and the method includes:
a reaction step of reacting
the sample,
a support including a first binding portion,
a reporter substance including a second binding portion,
a first trapping substance that includes a first binding partner portion capable of binding to the first binding portion and the second binding portion and that can bind to the target substance, and
a second trapping substance that includes a second binding partner portion capable of binding to the first binding portion and the second binding portion and that can bind to the target substance
to form a complex of "support—first trapping substance—target substance—second trapping substance—reporter substance" or a complex of "support—second trapping substance—target substance—first trapping substance—reporter substance"; and
a detection step of detecting a signal from the reporter substance in the complex.

In the present disclosure, the complex of "support—first trapping substance—target substance—second trapping substance—reporter substance" refers to a complex including the support, the first trapping substance, the target substance, and the second trapping substance, and in which the support, the first trapping substance, the target substance, the second trapping substance, and the reporter substance are directly or indirectly bound in this order. In the complex of "support—first trapping substance—target substance—second trapping substance—reporter substance," the support and the first trapping substance are directly or indirectly bound, the first trapping substance and the target substance are directly or indirectly bound, the target substance and the second trapping substance are directly or indirectly bound, and the second trapping substance and the reporter substance are directly or indirectly bound. As noted above, the first and second binding partner portions are capable of binding to the first and second binding portions. For the avoidance of doubt this does not refer to simultaneous binding, instead the binding partner portion is capable of binding to the first binding portion and separately, the second binding portion.

First Trapping Substance

In the first aspect, the "first trapping substance" includes a target substance recognition site via which the first trapping substance selectively binds to a target substance or binds to only a target substance, and the first binding partner portion that can bind to the first binding portion immobilized on the support.

Here, the trapping substance is not a substance trapped by a target substance, but a substance that traps a target substance via the target substance recognition site.

Examples of a substance that constitutes a target substance recognition portion include antibodies, low-molecular weight antibodies, peptides, and aptamers, and aptamers are preferable from the viewpoint of the time it takes to obtain a target substance recognition portion that corresponds to the target substance.

The first binding partner portion may be a portion that is originally included in the first trapping substance or a portion that is added thereto by chemical modification or the like. For example, an Fc site that is originally included in an antibody or a sugar chain can also be used as the first binding partner portion.

The aptamer may be a nucleic-acid aptamer or a peptide aptamer. The nucleic-acid aptamer may be formed of any type of nucleic acid, and examples of the nucleic acid include RNA, DNA, and modified products and analogs thereof. RNA is preferable.

In the first trapping substance, the target substance recognition portion and the first binding partner portion may be coupled to each other directly or via a linker. The first trapping substance may also be coupled in advance to the first binding portion immobilized on the support.

Second Trapping Substance

In the first aspect, the "second trapping substance" includes a target substance recognition site via which the second trapping substance selectively binds to a target substance or binds to only a target substance, and the second binding partner portion that can bind to the second binding portion included in the reporter substance.

Here, the trapping substance is not a substance trapped by a target substance, but a substance that traps a target substance via the target substance recognition site.

The second binding partner portion may be a portion that is originally included in the second trapping substance or a portion that is added thereto by chemical modification or the like. For example, an Fc site that is originally included in an antibody or a sugar chain can also be used as the second binding partner portion.

Examples of a substance that constitutes a target substance recognition portion include antibodies, low-molecular weight antibodies, peptides, and aptamers, and aptamers are preferable.

The aptamer may be a nucleic-acid aptamer or a peptide aptamer, and the nucleic-acid aptamer is preferable. The nucleic-acid aptamer may be formed of any type of nucleic acid, and examples of the nucleic acid include RNA, DNA, and modified products and analogs thereof. RNA is preferable.

In the second trapping substance, the target substance recognition portion and the second binding partner portion may be coupled to each other directly or via a linker. The second trapping substance may also be coupled in advance to the second binding portion immobilized on the reporter substance.

In one or more embodiments, examples of the bond between the first or second binding partner portion and the first or second binding portion include a bond between an antibody or an antigen binding site thereof and an antigen, a bond between avidin/streptavidin/neutravidin and biotin, a bond between dinitrophenol (DNP) and an anti-DNP antibody, a bond between digoxin and an anti-digoxin antibody, a bond between digoxigenin and an anti-digoxigenin antibody, a bond between a hapten and an anti-hapten, a bond between a polysaccharide and a polysaccharide binding site, a bond between lectin and a lectin receptor, a bond between a ligand and a ligand receptor, a bond between fluorescein and an anti-fluorescein antibody, and a bond between nucleic acids complementary to each other. A bond between nucleic acids complementary to each other is particularly preferable.

In one or more embodiments, examples of the binding partner portion include an antibody or an antigen binding site thereof, avidin, streptavidin, neutravidin, DNP digoxin, digoxigenin, a hapten, a polysaccharide, lectin, a ligand, fluorescein, and nucleic acids complementary to the first or second binding portion.

In one or more embodiments, examples of the binding portion include an antigen, biotin, an anti-DNP antibody, anti-digoxin antibody, an anti-digoxigenin antibody, an anti-hapten, a polysaccharide binding site, a lectin receptor, a ligand receptor, an anti-fluorescein antibody, and nucleic acids complementary to the binding partner portion.

The first binding partner portion and the second binding partner portion may be the same binding partner portion, and the first binding portion and the second binding portion may be the same binding portion. Thus, for example, the target substance can be changed by changing only the target substance recognition portion of the first trapping substance and the second trapping substance. The support and the reporter substance can be used as they are without changing.

The above-mentioned bonds are indirect bonds. The term "indirect bond" as used in the present disclosure refers to a hydrogen bond, an ionic bond, and a bond formed by non-covalent interaction such as hydrophobic interaction. On the other hand, in one or more embodiments, a direct bond refers to a covalent bond.

In one or more embodiments, when the target substance recognition portion is formed of a nucleic-acid aptamer, the binding partner portion can also be formed of a nucleic acid. In this case, the binding portion can also be formed of a nucleic acid that is complementary to the above-mentioned nucleic acid. In one or more embodiments, when the trapping substance is a nucleic-acid aptamer probe, examples of a combination of the binding partner portion and the binding portion include a combination of poly-A and poly-dT, and a combination of poly-U and poly-dA. In this case, when a nucleic-acid aptamer is obtained using the systematic evolution of ligands by exponential enrichment (SELEX) method, the obtained nucleic-acid aptamer can be applied to the detection method of the present disclosure as it is by designing a nucleic acid pool including sequences for the binding partner portion and random sequences, thus making it possible to reduce the examinations of conditions which allow candidate trapping substances to be selected. Therefore, this is particularly preferred.

It should be noted that, in the present disclosure, when both the binding partner portion and the binding portion are formed of nucleic acids whose sequences are complementary to each other, these sequences may be sequences that form strands that are completely complementary to each other, or sequences that do not form strands that are completely complementary to each other, as long as the binding partner portion and the binding portion can bind to each other.

Reaction Step

The reaction step in the present disclosure is a step of reacting the elements, namely the first trapping substance, the target substance, the second trapping substance, and the reporter substance (or a sub-set of these elements or complexes of these elements which have already been formed), with one another on the support to form a complex constituted by the elements in which the elements bind to one another. In one or more embodiments, the elements bind to one another due to non-covalent interaction. At this time, there is no particular limitation on the order of the elements in the complex, and a complex of "support—first trapping substance—target substance—second trapping substance—reporter substance" or a complex of "support—second trapping substance—target substance—first trapping substance—reporter substance" is formed, for example.

Detection Step

The detection step in the present disclosure is a step of detecting a signal from the target substance in the above-mentioned complex that has been formed on the support and immobilized thereon. One example of the signal from the target substance is fluorescence, which can be detected using a fluorescent immunochromatographic reader or the like, but there is no particular limitation thereto. The presence of a signal is indicative of the presence of the target substance in the sample.

In one or more embodiments, in the first detection method according to the present disclosure, the first binding partner portion can bind to the second binding portion (as well as the first binding portion), the second binding partner portion can bind to the first binding portion (as well as the second binding portion), a complex of "support—first trapping substance—target substance—second trapping substance—reporter substance" or a complex of "support—second trapping substance—target substance—first trapping substance—reporter substance" is formed in the reaction step, and the target substance is detected using the signal from the reporter substance in the complex in the detection step.

A single complex of "support—first trapping substance—target substance—second trapping substance—reporter substance" or a single complex of "support—second trapping substance—target substance—first trapping substance—reporter substance" includes two or more trapping substances, and these two or more trapping substances may be of the same type or of different types. Trapping substances of the same type (or a single type) have the same binding partner portion and the same target substance recognition portion. Preferably trapping substances of the same type are identical. Trapping substances of a different type have the same binding partner portions but different target substance recognition portions.

Complex Formation Order

When the complex of "support—first trapping substance—target substance—second trapping substance—reporter substance" is formed, a "support—first trapping substance" bond, a "first trapping substance—target substance" bond, a "target substance—second trapping substance" bond, and a "second trapping substance—reporter substance" bond are formed. These bonds may be formed in any order, or these bonds may be formed simultaneously. The same applies to the case where the complex of "support—second trapping substance—target substance—first trapping substance—reporter substance" is formed.

In one or more embodiments, in the first detection method according to the present disclosure, the first trapping substance and the second trapping substance are the same, and these same trapping substances can bind to the target substance at different positions of the target substance.

In one or more embodiments, in the first detection method according to the present disclosure, the first trapping substance binds to the first binding portion included on the support.

Support

In one or more embodiments, examples of the support include membranes made of nitrocellulose, nylon, polyamide, paper, and glass fibers, and a specific example thereof is a membrane for immobilizing a lateral flow-type immuno chromatographic strip (test piece) (this membrane is also referred to as a reaction membrane).

The support according to the present disclosure includes the first binding portion. In some instances reference is made to a binding portion being immobilized on the support. Also in these cases, the binding portion forms part of the support. In one or more embodiments, the first binding portion is immobilized using an immobilization means such as a chemical covalent bond or a covalent bond formed with physical energy caused by UV irradiation.

Reporter Substance

A reporter substance (detection reagent) used in immuno chromatography can be used as the reporter substance. In one or more embodiments, examples thereof include enzymes, ferritin, fluorescent light-absorbing silica particles, fluorescent light-absorbing latex particles, semiconductor minute particles, and gold colloid particles. The reporter substance according to the present disclosure includes the second binding portion. In some instances reference is made to a binding portion being immobilized on the reporter substance. Also in these cases, the binding portion forms part of the reporter substance. A binding portion probe can be immobilized on the reporter substance as appropriate.

A method for obtaining a signal from the reporter substance can be selected as appropriate depending on the reporter substance. In the case of a reporter substance that produces fluorescence, emits light, or develops a color, a signal can be detected or recorded visually or using an appropriate reader or imaging device, and analyzed as needed. Other methods of detecting the signal from the reporter substance include, in one or more embodiments, a microscope, a spectrophotometer, a colorimeter, and the like.

Target Substance

In one or more embodiments, examples of the target substance include antibodies, DNA, RNA, sugars, sugar chains, ligands, receptors, peptides, proteins, chemical substances, pathogens, and parts thereof. Examples of a sample containing the target substance include, but are not particularly limited to, body fluids such as serum, blood, plasma, saliva, urine, tears, and nasal fluids, cell culture solutions, food-derived samples for an analysis of residual agricultural chemicals, aqueous samples for an analysis of water quality, and diluted products thereof.

The first detection method according to the present disclosure can be used for an immuno chromatographic method, an ELISA method, a flow-through method, an SPR method, a beads assay method, and the like.

The immuno chromatographic method according to the present disclosure generally refers to measurement methods in which a capillary phenomenon in the support is utilized. In one or more embodiments, the immuno chromatographic method includes a lateral-flow detection method. The immuno chromatographic method according to the present disclosure also encompasses detection methods in which the principle of how a target substance is trapped by a trapping substance is not based on an immune reaction. For example, the immuno chromatographic method according to the present disclosure encompasses a detection method in which an aptamer probe is used as the trapping substance.

First Detection System

Another aspect of the present disclosure relates to a target substance detection system for performing the above-mentioned method for detecting a target substance in a sample. In one or more embodiments, a first detection system according to the present disclosure includes: a support including a first binding portion; a reporter substance including a second binding portion; a first trapping substance that includes a first binding partner portion capable of binding to the first binding portion and the second binding portion and that can bind to the target substance; and a second trapping substance that includes a second binding partner portion capable of binding to the first binding portion and the second binding portion and that can bind to the target substance.

The first detection system according to the present disclosure can be used for the first detection method according to the present disclosure.

Second Aspect

The second aspect according to the present disclosure is an embodiment in the case where, in the first aspect, the binding partner portion of the trapping substance can bind to both the binding portion of the support and the binding portion of the reporter substance, an immuno chromatographic detection method is used as the detection method, and the target substance recognition portion is formed of an aptamer.

The second aspect according to the present disclosure is based on the fact that the following problems are found in the immuno chromatographic detection method in which aptamers are used and the binding locations of the aptamers are limited to the immobilization side (support side) and the detection side (reporter substance side), that is, an aptamer for the immobilization side (support side) and an aptamer for the detection side (reporter substance side) are used.

1. Problem in Aptamer Design (1) As in the case of antibodies, there is a possibility that some aptamers are suitable for use on the detection side (reporter substance side) and others are suitable for use on the immobilization side (support side).

(2) With the conventional immuno chromatographic detection method, it is necessary to prepare two types of aptamers, namely an aptamer for the immobilization side (support side) and an aptamer for the detection side (reporter substance side), in the step of obtaining aptamers, which leads to an increase in cost and time.

For example, when nucleic-acid aptamers are obtained by using a method such as a SELEX method, a plurality of types of aptamers (that are different in the sequences of regions for trapping a detection-target substance (target substance), but have the same binding partner sequence) can be obtained, but when aptamers having two types of binding partner sequences, namely the sequences of binding partners for the immobilization side (support side) and the detection side (reporter substance side), are needed, a step of adding, to one of two different types of candidate aptamer sequences, a binding partner sequence different from that included in the other type is needed.

That is, when binding to the support (or the reporter), a complex of "aptamer for immobilization side—target substance—aptamer for detection side" has a poorer reaction efficiency than a complex of "aptamer capable of binding to both immobilization side and detection side—target substance—aptamer capable of binding to both immobilization side and detection side."

2. Problem in Reaction Efficiency

The binding portions of an aptamer that binds to the reporter substance and an aptamer that binds to the support are limited, and therefore, when complexes of "aptamer—target substance—aptamer" bind to the reporter substance and the support, the reaction efficiencies decrease.

One aspect of the second detection method according to the present disclosure is a method for detecting a target substance in a sample using an immuno chromatographic method in which aptamer probes including an aptamer portion that can bind to the target substance and a binding partner portion that can bind to both a binding portion immobilized on the support and a binding portion immobilized on the reporter substance are used.

With the second detection method according to the present disclosure, in one or more embodiments, an immuno chromatographic detection method can be performed without preparing two types of aptamer probes whose binding directions each are limited to a direction toward the immobilization side (support side) or a direction toward the detection side (reporter substance side).

Aptamer Probe

In the second aspect according to the present disclosure, the "aptamer probe" includes an aptamer portion (target substance recognition portion) serving as an aptamer that binds to a target substance, and a binding partner portion that can bind to both a binding portion immobilized on the support and a binding portion immobilized on the reporter substance.

In the aptamer probe, the aptamer portion and the binding partner portion may be coupled to each other directly or via a linker.

The aptamer in the aptamer portion may be a nucleic-acid aptamer or a peptide aptamer. The nucleic-acid aptamer may be formed of any type of nucleic acid, and examples of the nucleic acid include RNA, DNA, and modified products and analogs thereof. In one aspect, RNA is a preferred nucleic acid for forming an aptamer.

The binding partner portion can bind to both the binding portion immobilized on the support and the binding portion immobilized on the reporter substance.

The binding portion immobilized on the support and the binding portion immobilized on the reporter substance may be the same as or different from each other as long as the binding partner portion can bind thereto.

The binding partner portion can be considered a tag portion coupled to the aptamer.

In one or more embodiments, examples of the combination of the binding portion and the binding partner portion (the combination of the binding partner portion and the binding portion) include a combination of an antibody or low-molecular antibody and a target substance, a combination of avidin/streptavidin/neutravidin and biotin, a combination of dinitrophenol (DNP) and an anti-DNP antibody, a combination of digoxin and an anti-digoxin antibody, a combination of digoxigenin and an anti-digoxigenin antibody, a combination of a hapten and an anti-hapten, a combination of a polysaccharide and a polysaccharide binding site, a combination of lectin and a lectin receptor, a combination of a ligand and a ligand receptor, a combination of fluorescein and an anti-fluorescein antibody, and a combination of nucleic acids complementary to each other.

The binding portion and the binding partner portion is as described above.

In one or more embodiments, when the aptamer portion is formed of a nucleic acid, the binding partner portion can also be formed of a nucleic acid. In this case, the binding portion can also be formed of a nucleic acid that is complementary to the above-mentioned nucleic acid of the binding partner portion. In one or more embodiments, in the case of a nucleic-acid aptamer probe, examples of a combination of the binding partner portion and the binding portion include a combination of poly-A and poly-dT, and a combination of poly-U and poly-dA.

Binding Portion Probe

When the support or reporter substance does not initially include the binding portion, a binding portion can be immobilized using a binding portion probe. In one or more embodiments, the binding portion probe includes a binding portion, and a functional group that can be subjected to a reaction of binding or crosslinking to the support or reporter substance. In addition, in one or more embodiments, the binding portion probe may include a linker between the binding portion and the functional group.

It should be noted that, in the present disclosure, in the case where the support itself originally includes a binding portion, the "binding portion immobilized on the support" also encompasses this binding portion. Similarly, in the case where the reporter substance itself originally includes a binding portion, the "binding portion immobilized on the reporter substance" also encompasses this binding portion.

In one or more embodiments, examples of the functional group include an amino group, a carboxyl group, an NHS ester group, an imide ester group, a maleimide group, haloacetic acid, a piridyl disulfide group, a sulfhydryl group, an aldehyde group, a hydrazide group, and alkoxyamine group.

When the support is a nitrocellulose membrane or another analysis membrane, and the binding portion is formed of DNA, the above-mentioned functional group can be an amino group. The binding portion probe can be immobilized on the support by arranging a DNA modified with an amino group (binding portion probe) on the support and irradiating the DNA with UV (Bruno, Pathogens. 2014 June; 3(2); 341-355).

When the reporter substance includes latex particles, and the binding portion is formed of DNA, the above-mentioned functional group can be an amino group. A carboxyl-amine crosslink can be formed by activating the carboxyl groups on the surfaces of the latex particles with carbodiimide or the like.

However, the method for binding the binding portion probe to the support or reporter substance and form a crosslink is not limited thereto, and a crosslinking method can be selected as appropriate, and thus a functional group can be selected depending on the crosslinking method.

Support

A membrane in which a developing solution can be developed and on which the binding portion probe can be immobilized can be used as the support. In one or more embodiments, examples of such a membrane include membranes made of nitrocellulose, nylon, polyamide, paper, and glass fibers, and a specific example thereof is a membrane for immobilizing a lateral flow-type immuno chromatographic strip (test piece) (this membrane is also referred to as a reaction membrane). In one or more embodiments, a nitrocellulose membrane can be used as the support.

Reporter Substance

A reporter substance (detection reagent) used in immuno chromatography can be used as the reporter substance. In one or more embodiments, the reporter substance includes enzymes, ferritin, fluorescent light-absorbing silica particles, fluorescent light-absorbing latex particles, semiconductor minute particles, and gold colloid particles. The binding portion probe can be immobilized on (and form part of) the reporter substance as appropriate.

A method for obtaining a signal from the reporter substance can be selected as appropriate depending on the reporter substance. In the case of a reporter substance that produces fluorescence, emits light, or develops a color, a signal can be detected or recorded visually or using an appropriate reader or imaging device, and analyzed as needed.

Target Substance

In one or more embodiments, examples of the target substance include antigens, antibodies, DNA, RNA, sugars, sugar chains, ligands, receptors, peptides, proteins, chemical substances, pathogens, and parts thereof. Examples of a sample containing the target substance include, but are not particularly limited to, body fluids such as serum, blood, plasma, saliva, urine, tears, and nasal fluids, cell culture solutions, food-derived samples for an analysis of residual agricultural chemicals, aqueous samples for an analysis of water quality, and diluted products thereof.

Immuno Chromatographic Detection Method

One aspect of the second detection method according to the present disclosure is a detection method based on the immuno chromatographic method in which the one or more of the above-described aptamer probes according to the present disclosure are used, and includes trapping the target substance and the reporter substance on the support in a binding state represented as the "support—aptamer probe—target substance—aptamer probe—reporter substance." As referred to herein "trapping" refers to fixing the target substance and the reporter substance to the support via the intermediacy of the trapping substances (e.g. aptamers).

In other words, one aspect of the second detection method according to the present disclosure is a detection method based on the immuno chromatographic method in which the above-described aptamer probes according to the present disclosure are used, and includes forming a complex of "support—aptamer probe—target substance—aptamer probe—reporter substance" on the support.

A complex of "support—aptamer probe—target substance—aptamer probe—reporter substance" is formed on a detection region (a portion of the support on which the binding portion is immobilized) of an immuno chromatographic test piece after a developing solution flows, and if a signal from the reporter substance is detected, this means that the target substance in the sample is detected.

Accordingly, one aspect of the second detection method according to the present disclosure further includes detecting a signal from the reporter substance.

Embodiment in which Two or More Types of Aptamer Probes are Used (Embodiment 1)

In one or more embodiments of the second detection method according to the present disclosure, two or more types of aptamer probes can be used. As referred to herein aptamer probes of a different type have the same binding partner portions but different target substance recognition portions, i.e. different aptamer portions. In methods using such aptamers more than one aptamer probe is used in the method.

This embodiment will be described with reference to the schematic view shown in FIG. 1. This embodiment is a method in which two different types of aptamer probes 4 and 7 are used. Aptamer probes 4 and 7 have different aptamer portions, and these aptamer portions can bind to different portions of a target substance 6. The aptamer probes 4 and 7 include a common binding partner portion 5. In other words, the aptamer probes 4 and 7 include the same binding partner portion 5. A binding portion 3 is immobilized on a reporter substance 1 via a binding portion probe 2. The binding portion 3 is also immobilized on a support 11 via a binding portion probe 10. That is, the reporter substance 1 and the support 11 include the same binding portion 3. Both the aptamer probes 4 and 7 can bind to both the reporter substance 1 and the support 11 due to the binding partner portion 5 and the binding portion 3 binding to each other.

Focusing on a complex of "aptamer probe 4—target substance 6—aptamer probe 7", two binding partner portions 5 can bind to the support 11, and therefore, it can be thought that the efficiency of trapping the complex on the support increases compared with the case where the aptamer probes 4 and 7 include different binding partner portions 5.

Embodiment in which One Type of Aptamer Probe is Used (Embodiment 2)

In one or more embodiments of the second detection method according to the present disclosure, one type of aptamer probe can be used. As referred to herein aptamer probes of the same type (or single aptamers) have the same binding partner portion and the same target substance recognition portion, i.e. aptamer portion. Preferably aptamer probes of the same type are identical. In methods using such aptamers the method may be performed using just one aptamer.

Figure 2:
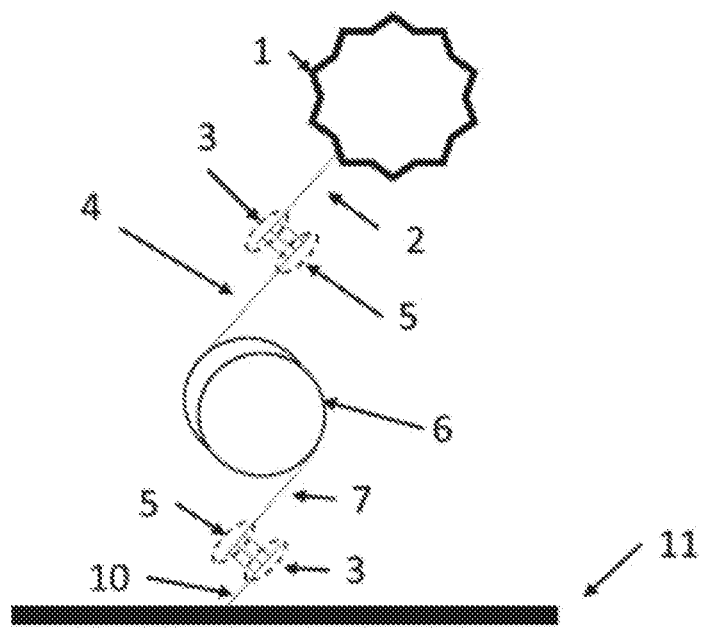
FIG. 2 is a schematic view of an embodiment of the second aspect, illustrating a state in which a reporter substance 1 and a target substance 6 are trapped on a support 11 via aptamer probes 4 and 7 that are of the same type. The aptamer probes 4 and 7 have the same aptamer portion and the same binding partner portion 5. The target substance 6 is a (polyvalent) substance to which a plurality of aptamers of the same type can bind. The binding partner portion 5 can bind to both a binding portion 3 of a binding portion probe 2 immobilized on the reporter substance 1 and a binding portion 3 of a binding portion probe 10 immobilized on the support 11. At this time, the binding portion 3 and the binding partner portion 5 indirectly (i.e. non-covalently) bind to each other, and the aptamer probes 4 and 7 are indirectly immobilized on the reporter substance 1 or the support 11.

This embodiment will be described with reference to the schematic view shown in FIG. 2. In the method of this embodiment, a plurality of aptamers of the same type can bind to a target substance (a multimer complex including two or more elements is formed, for example), and aptamer probes 4 and 7 of the same type are used. The aptamer probes 4 and 7 include the same aptamer portion and the same binding partner portion 5. Both the aptamer probes 4 and 7 can bind to both a reporter substance 1 and a support 11 due to the binding partner portion 5 and the binding portion 3 binding to each other.

Focusing on a complex of "aptamer probe 4—target substance 6—aptamer probe 7", two binding partner portions 5 can bind to the support 11 in the same manner as in Embodiment 1, and therefore, it can be thought that the efficiency of trapping the complex on the support is increased compared with the case where the aptamer probes 4 and 7 include different binding partner portions 5.

Embodiment in which One-Component Developing Solution is Used (Embodiment 3)

In one or more embodiments of the second detection method according to the present disclosure, a developing solution containing a sample, aptamer probes, and a reporter substance can be developed in a detection region (a portion of a support on which a binding portion is immobilized) of an immuno chromatographic test piece. As referred to herein developing refers to allowing the elements which are brought into contact to form a complex when the relevant binding partners are present.

In this embodiment, the aptamer probes may be those of the embodiment (Embodiment 1) in which two or more types of aptamer probes are used or those of the embodiment (Embodiment 2) in which one type of aptamer probe is used.

With this embodiment, the second detection method according to the present disclosure can be performed using one type of developing solution.

Embodiment in which Two-Component Developing Solution is Used (Embodiment 4)

In one or more embodiments of the second detection method according to the present disclosure, a configuration can be employed in which a developing solution containing a sample and aptamer probes (a developing solution containing no reporter substance) is first developed in a detection region (a portion of a support on which a binding portion is immobilized) of an immuno chromatographic test piece, and then a developing solution containing a reporter substance is developed in the detection region.

In this embodiment, the aptamer probes may be those of the embodiment (Embodiment 1) in which two or more types of aptamer probes are used or those of the embodiment (Embodiment 2) in which one type of aptamer probe is used.

With this embodiment, a complex of "aptamer probe—target substance—aptamer probe" can be brought into contact with the detection region (a portion of a support on which a binding portion is immobilized) before the reporter substance is brought into contact therewith. It is thus thought that the efficiency of trapping the complex on the detection region can be increased, for example.

Second Detection System

Another aspect of the present disclosure relates to a target substance detection system using an immuno chromatographic method. A second detection system according to the present disclosure includes: an immuno chromatographic test piece including a detection region on which a binding portion is immobilized; a reporter substance on which a binding portion is immobilized; and the aptamer probes according to the present disclosure.

The second detection system according to the present disclosure can be used to perform the second detection method according to the present disclosure.

In the second detection system according to the present disclosure, the reporter substance and the aptamer probes may be separate from the immuno chromatographic test piece and be contained together or individually in the developing solution. The reporter substance and the aptamer probes may also be arranged on the immuno chromatographic test piece in the dry state.

The reporter substance and the aptamer probes may also be arranged on the immuno chromatographic test piece in the state in which they are contained together or individually in the developing solution.

Second Detection Kit

Another aspect of the present disclosure relates to a kit for performing the second detection method according to the present disclosure. A second detection kit according to the present disclosure includes: an immuno chromatographic test piece including a detection region on which a binding portion is immobilized; a reporter substance on which a binding portion is immobilized; and the aptamer probes according to the present disclosure.

In the second detection kit according to the present disclosure, the reporter substance and the aptamer probes may be separate from the immuno chromatographic test piece and be contained together or individually in the developing solution.

The reporter substance and the aptamer probes may also be arranged on the immuno chromatographic test piece in the dry state.

The reporter substance and the aptamer probes may also be arranged on the immuno chromatographic test piece in the state in which they are contained together or individually in the developing solution.

The present disclosure can relate to the following one or more embodiments that are not limited.

[1] A method for detecting a target substance in a sample, including:
a reaction step of reacting, with one another,
the sample,
a support including a first binding portion,
a reporter substance including a second binding portion,
a first trapping substance that includes a first binding partner portion capable of binding to the first binding portion and the second binding portion and that binds to the target substance, and
a second trapping substance that includes a second binding partner portion capable of binding to the first binding portion and the second binding portion and that binds to the target substance
to form a complex of "support—first trapping substance—target substance—second trapping substance—reporter substance" or a complex of "support—second trapping substance—target substance—first trapping substance—reporter substance"; and
a detection step of detecting a signal from the reporter substance in the complex.

[2] The method according to [1], wherein the first trapping substance and/or the second trapping substance is an aptamer probe.

[3] The method according to [1] or [2], wherein the aptamer probe is a nucleic-acid aptamer.

[4] The method according to any one of [1] to [3], wherein all bonds between the first or second binding partner portion and the first or second binding portion are bonds formed by non-covalent interaction.

[5] The method according to [4], wherein the bonds formed by non-covalent interaction are bonds between nucleic acids complementary to each other.

[6] The method according to any one of [1] to [5], wherein the first trapping substance and the second trapping substance are the same, and the target substance binds to the first trapping substance and the second trapping substance at different positions of the target substance.

[7] The method according to any one of [1] to [6], wherein detection is performed using an immuno chromatographic method.

[8] The method according to any one of [1] to [7], wherein the first trapping substance binds to the first binding portion included on the support.

[9] The method according to any one of [1] to [8], including developing the sample, the first trapping substance, the second trapping substance, and the reporter substance on the support.

[10] The method according to [8] or [9], including:
reacting the sample, the support, the first trapping substance, and the second trapping substance with one another to form a complex of "support—first trapping substance—target substance—second trapping substance" or a complex of "support—second trapping substance—target substance—first trapping substance," and
reacting the formed complex and the reporter substance with each other.

[11] A target substance detection system for performing the method according to any one of [1] to [10].

[12] A method for detecting a target substance in a sample using an immuno chromatographic method, including:
using an aptamer probe including an aptamer portion that binds to the target substance, and a binding partner portion that binds to both a binding portion immobilized on a support and a binding portion immobilized on a reporter substance
to trap the target substance and the reporter substance on the support in a binding state represented as "support—aptamer probe—target substance—aptamer probe—reporter substance"; and
detecting a signal from the reporter substance. Such methods may be performed according to any one of [1] to [10], wherein said method uses an immuno chromatographic method and one or more aptamer probe (which may the same type or a different type).

[13] The method according to [12], wherein two or more types of aptamer probes that capable of binding to different portions of the target substance are used as the aptamer probe.

[14] The method according to [12], wherein the target substance binds to the same portion of the aptamer portions at different positions of the target substance.

[15] The method according to any one of [12] to [14], including developing a liquid containing a sample, the aptamer probe, and the reporter substance in the support on which the binding portion is immobilized.

[16] The method according to any one of [12] to [14], including:
developing a liquid containing a sample and the aptamer probe in the support on which the binding portion is immobilized; and
developing a liquid containing the reporter substance on the support.

[17] A target substance detection system in which an immuno chromatographic method is used, including:
an immuno chromatographic test piece including a detection region on which a binding portion is immobilized;
a reporter substance on which a binding portion is immobilized; and
an aptamer probe including a binding partner portion that binds to both the binding portion of the detection region and the binding portion of the reporter substance, and an aptamer portion that binds to the target substance. The system may be according to [11] for use with an immuno chromatographic method

[18] A kit for performing the method according to any one of [12] to [16], including:
an immuno chromatographic test piece including a detection region on which a binding portion is immobilized;
a reporter substance on which a binding portion is immobilized; and
an aptamer probe including a binding partner portion that binds to both the binding portion of the detection region and the binding portion of the reporter substance, and an aptamer portion that binds to the target substance. One or more aptamer probe may be used which may be the same type or a different type.

Hereinafter, the present disclosure will be more specifically described by way of examples, but these examples are merely exemplary, and the present disclosure is not limited to these examples.

EXAMPLES

Example 1

Immuno Chromatographic Detection Method in which Two Types of Nucleic-Acid Aptamer Probes are Used Binding portion probes including a binding sequence were immobilized on a reporter substance and a nitrocellulose membrane, and A/Panama/2007/1999 (H3N2) hemagglutinin (referred to as "HA" hereinafter) was detected using nucleic-acid aptamers that recognize A/Panama/2007/1999 (H3N2) HA.

It should be noted that, in the description below, A/Panama/2007/1999 (H3N2) HA may be abbreviated as H3/Panama or H3. HA refers to a hemagglutinin protein called an HA protein that is present on an envelope of an influenza virus.

Figure 3:
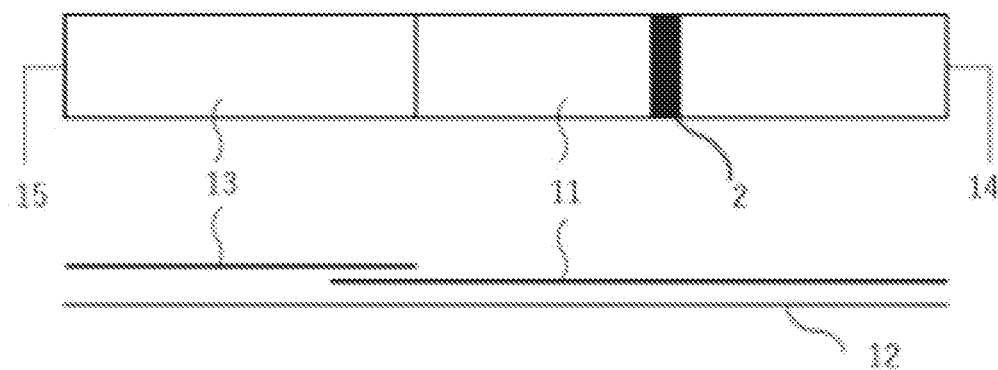
FIG. 3 is a schematic view of an immuno chromatographic test piece used in an embodiment.

1. Production of Immuno Chromatographic Test Piece on which Single-Stranded Polynucleotide is Immobilized 1-1. Production of Immuno Chromatographic Test Piece An immuno chromatographic test piece having a configuration as shown in FIG. 3 was produced. A nitrocellulose membrane (support) 11, a backing sheet 12, and an absorption strip 13 were bonded together and cut along the longi-tudinal axis direction such that the width was 3.9 mm, and thus an immuno chromatographic test piece was produced.

1-2. Production of Immuno Chromatographic Test Piece on which Single-Stranded Polynucleotide is Immobilized A modified polynucleotide having a sequence (SEQ ID NO: 1) below was used as a binding portion probe and diluted to a concentration of 500 µM using Nuclease Free water, and thus a binding portion probe solution was prepared. The 5' terminus of the probe was modified with an amino group via a linker. The underlined sequence corresponds to a first binding portion to be immobilized on a support, and is complementary to the sequence of a binding partner portion included in a nucleic-acid aptamer probe, which will be described later.

Sequence of single-stranded polynucleotide (2):
(SEQ ID NO: 1)
5'-[NH$_2$]TTTTTTTTTTTTTTTTTTTTTTT-3'

Then, 0.1 µL of the binding portion probe solution was dropped on the immuno chromatographic test piece produced in (1-1) above at a position (a portion denoted by reference numeral 2 in FIG. 3) 1.4 cm away from one end 14 on the nitrocellulose membrane side (this end is taken as an upstream end 14 and the end on the opposite side is taken as a downstream end 15 in FIG. 3). The immuno chromatographic test piece on which the binding portion probe solution had been dropped was irradiated with ultraviolet light (254 nm) at about 1000 mJ/cm$^2$ using a UV irradiation apparatus (UVGL-58) manufactured by UVP, and thus the binding portion probe was immobilized on the membrane 11 (at a portion denoted by reference numeral 2 in FIG. 3).

2. Production of Fluorescent Latex Particles on which Polynucleotide is Immobilized 2-1. Activation of Fluorescent Latex Particles 1-[3-(Dimethylamino)propyl]-3-ethylcarbodiimide (referred to as "EDC" hereinafter) and N-hydroxysuccinimide (referred to as "NHS" hereinafter) were diluted with a 2-morpholinoethanesulfonic acid (referred to as "MES" hereinafter) buffer solution to prepare a 10-mg/mL solution and 50-mg/mL solution, respectively, to be used to activate the carboxyl groups on fluorescent latex particles. To 215.5 µL of a MES buffer solution, 119.5 µL of an EDC solution and 115 µL of an NHS solution were added, and a 1%-solid solution of fluorescent latex particles manufactured by Thermo (Fluoro-Max™ Dyed Carboxylate-Modified Microparticles) was further added thereto. Then, the obtained mixture was mixed well using a vortex mixer. The mixed solution was set in a shaker and underwent a reaction for 30 minutes at room temperature. After the reaction, the fluorescent latex particles were centrifuged at 18, 300×g for 15 minutes, and the supernatant was removed. To the residual pellet-like fluorescent latex particles, 500 µL of a new MES buffer solution was added, and the pellets were resuspended using a vortex mixer and an ultrasonic cleaner. The washing operation was repeated twice in the same manner, and thus a fluorescent latex particle solution obtained by suspending the fluorescent latex particles in 500 µL of a MES buffer solution was prepared.

2-2. Sensitization of Fluorescent Latex Particles to Single-Stranded Polynucleotide A modified polynucleotide having a sequence (SEQ ID NO: 1) below was used as a binding portion probe and diluted to a concentration of 16 μM using Nuclease Free water, and thus a binding portion probe solution was prepared. The 5' terminus of the bonding portion probe was modified with an amino group via a linker. The underlined sequence corresponds to a second binding portion to be immobilized on the fluorescent latex, which is a reporter substance, and is complementary to the sequence of a binding partner portion included in a nucleic-acid aptamer probe, which will be described later. A first binding portion probe and a second binding portion probe have the same sequence configuration in which twenty-four T's are linearly coupled.

```
Sequence of single-stranded polynucleotide (2):
                                          (SEQ ID NO: 1)
5'-[NH₂]TTTTTTTTTTTTTTTTTTTTTTTT-3'
```

To the fluorescent latex particle solution prepared in (2-1) above, 200 μL of the binding portion probe solution was added, and the obtained mixture was mixed using Vortex. The mixed solution was set in a shaker and underwent a reaction for 60 minutes at room temperature. After the reaction, the fluorescent latex particles were centrifuged at 18,300×g for 15 minutes, and the supernatant was removed. To the residual pellet-like fluorescent latex particles, 500 μL of a new Tris-HCl buffer solution was added, and the pellets were resuspended using a vortex mixer and an ultrasonic cleaner. The washing operation was repeated twice in the same manner, and thus a solution of the fluorescent latex particles that had been sensitized to the single-stranded polynucleotide (binding portion) obtained by suspending these fluorescent latex particles in 500 μL of a Tris-HCl buffer solution was prepared. Particles sensitized to the single-stranded polynucleotide are particles on which the single-stranded polynucleotide are immobilized.

3. Detection of H3

3-1. Preparation of Developing Solution Containing HA

As described below, 70 μL of a developing solution containing HA was prepared on a 96-well plate.
- 0.5 mg/mL HA solution
- 0.5 μL of fluorescent latex particles sensitized to single-stranded polynucleotide (binding portion)
- 0.5 μL of two types of nucleic-acid aptamer probes (0.25 μL each)
- 69 μL of developing solution The HA solution was a solution containing H3 as a detection-target substance (target substance) or a solution containing A/California/06/2009 (H1N1) recombinant HA (referred to as "H1" hereinafter) as a negative control. The fluorescent latex particles sensitized to the single-stranded polynucleotide were fluorescent latex particles on which the single-stranded DNA (binding portion) having the sequence shown in (2-1) and (2-2) above was immobilized. The used nucleic-acid aptamer probes were formed of RNAs, and the sequences thereof were as shown below. The underlined portions indicate sequences (binding partner portions) complementary to those of the binding portions.

In other words, a nucleic-acid aptamer probe 1 and a nucleic-acid aptamer probe 2 correspond (i.e. bind to) to the first trapping substance and the second trapping substance, respectively. A first binding partner portion of the nucleic-acid aptamer probe 1 and a second binding partner portion of the nucleic-acid aptamer probe 2 have the same sequence configuration in which twenty-four A's are linearly coupled. That is, the first binding partner portion having a sequence in which twenty-four A's are linearly coupled can form a strand complementary to and bind to both the first binding portion of the support and the second binding portion of the reporter substance (the above-mentioned fluorescent latex particles) that have a sequence in which twenty-four T's are linearly coupled. Similarly, the second binding partner portion having a sequence in which twenty-four A's are linearly coupled can also form a strand complementary to and bind to both the first binding portion of the support and the second binding portion of the reporter substance. In this example, a sequence that forms a strand that is completely complementary to the first binding partner portion and the second binding partner portion were used as the sequences of the first binding portion and the second binding portion, but the first binding portion and the second binding portion do not necessarily have a sequence for forming a strand that is completely complementary to the first binding partner portion as long as the first binding partner portion can bind to both the first binding portion and the second binding portion. Similarly, the first binding portion and the second binding portion do not necessarily have a sequence for forming a strand that is completely complementary to the second binding partner portion as long as the second binding partner portion can bind to both the first binding portion and the second binding portion.

```
Nucleic-acid aptamer probe 1:
                                          (SEQ ID NO: 2)
5'-GGGAGAAUUCCGACCAGAAGAAUAGUAGAAUGAGCUCUGUCGGACC

CAGCCUUUCCUCUCUCCUUCCUCUUCUUUAAAAAAAAAAAAAAAAAAAA

AAAA-3'

Nucleic-acid aptamer probe 2:
                                          (SEQ ID NO: 3)
5'-GGGUUAGCAGUCGGCAUGCGGUACAGACAGACCCUUUAAAAAAAAA

AAAAAAAAAAAAAAA-3'
```

3-2. Detection of H3

After the front end of the immuno chromatographic test piece produced in (1-1) and (1-2) above was immersed in the developing solution containing H3 prepared in (3-1) above, and the test piece absorbed the developing solution containing H3 for 10 minutes, visual confirmation was performed using UVP UVGL-25 (95-0021-13) manufactured by Analytik Jena, and color development was confirmed using a fluorescent immunochromatographic reader (developed by ARKRAY Inc.).

4. Results

Figure 4:
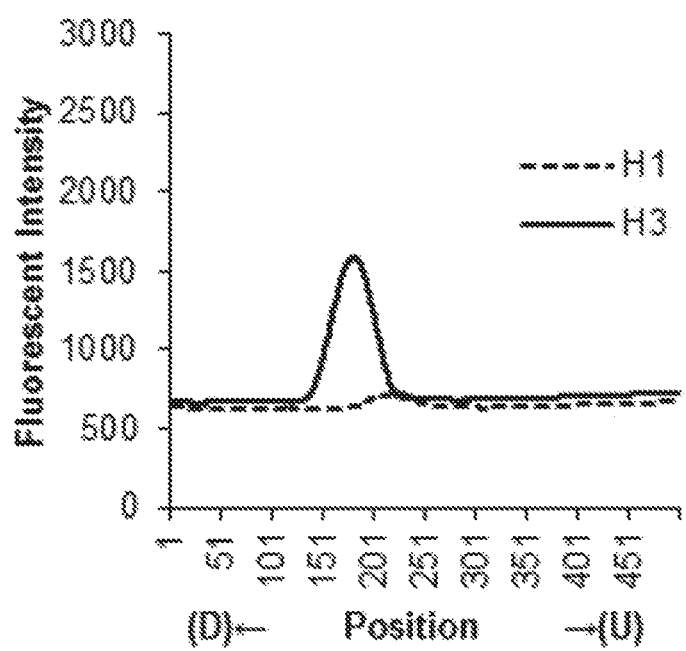
FIG. 4 is a graph illustrating an example of the result obtained by detecting an H3 protein using the second detection method according to the present disclosure in which two types of aptamer probes were used.

FIG. 4 shows the results of the measurements using the fluorescent immunochromatographic reader, indicating whether or not H3 was detected on the immuno chromatographic test piece. The vertical axis indicates the intensities of fluorescent signals that appeared on the immuno chromatographic test piece, and the horizontal axis indicates the positions on the nitrocellulose membrane on the immuno chromatographic test piece when the right side of the graph is taken as the upstream end. (U) indicates the upstream side, and (D) indicates the downstream side.

As shown in FIG. 4, when the developing solution containing H3 was used, the fluorescent signal was confirmed at the position at which the single-stranded polynucleotide (binding portion) was immobilized, whereas, when the developing solution containing no H3 was used, a fluorescent signal was not detected. It was shown from these results that the intended detection-target substance H3 could be trapped by using the immuno chromatographic test piece on which a strand (binding portion) complementary to a nucleic-acid aptamer was immobilized and the fluorescent latex particles on which the same complementary strand as the complementary strand immobilized on the test piece was immobilized.

Example 2

Immuno Chromatographic Detection Method in which One Type of Nucleic-Acid Aptamer Probe is Used The detectability of an immuno chromatographic detection method in which a detection-target substance having a trimeric structure is set as the target substance and only one type of nucleic-acid aptamer probe is used was tested. It should be noted that HA is a protein that forms a homotrimer.

1. Production of Immuno Chromatographic Test Piece on which Single-Stranded Polynucleotide is Immobilized An immuno chromatographic test piece on which a sequence (i.e., binding portion) complementary to the binding partner portion of the nucleic-acid aptamer probe was immobilized was prepared using the same method as that described in (1-1) and (1-2) of Example 1. However, the immobilization of the single-stranded polynucleotide by UV irradiation was performed as follows. That is, the single-stranded polynucleotide was irradiated with ultraviolet light (254 nm) at about 120 mJ/cm$^2$ using a UV irradiation apparatus (UVP CL-100) manufactured by Analytik Jena US, and then was dried at 40° C. for 5 to 10 minutes. Thus, the single-stranded polynucleotide was immobilized.

2. Production of Fluorescent Latex Particles on which Polynucleotide is Immobilized Fluorescent latex particles on which the binding portion was immobilized were prepared using the same method as that described in (2-1) and (2-2) of Example 1.

3. Evaluation of Multimer Detectability Using Only One Type of Nucleic-Acid Aptamer 3-1. Preparation of Developing Solution Containing HA As described below, 70 μL of a developing solution containing HA was prepared on a 96-well plate.
HA solution (containing H3 in a concentration of 2.5 μg/mL or no H3)
0.5 μL of fluorescent latex particles sensitized to single-stranded polynucleotide 0.25 μL of one type of nucleic-acid aptamer probe
69.25 μL of developing solution The HA solution was a solution containing H3 as a detection-target substance or a solution containing no H3. The fluorescent latex particles sensitized to the single-stranded polynucleotide were fluorescent latex particles on which the single-stranded DNA (binding portion) having the sequence shown in (2-1) and (2-2) of Example 1 above.

The used nucleic-acid aptamer was an RNA aptamer, and the sequence thereof was as shown below. The underlined portion indicates a sequence (binding partner portion) complementary to that of the binding portion.

Nucleic-acid aptamer probe 2:
(SEQ ID NO: 3)
5'-GGGUUAGCAGUCGGCAUGCGGUACAGACAGACCCUUU<u>AAAAAAAAA</u>
<u>AAAAAAAAAAAAAAA</u>-3'

3-2. Detection of H3

After the front end of the immuno chromatographic test piece produced in (1-1) and (1-2) above was immersed in the developing solution containing H3 prepared in (3-1) above, and the test piece absorbed the H3 developing solution for 10 minutes, visual confirmation was performed using UVP UVGL-25 (95-0021-13) manufactured by Analytik Jena, and color development was confirmed using a fluorescent immunochromato reader (developed by ARKRAY Inc.).

4. Results

Figure 5:
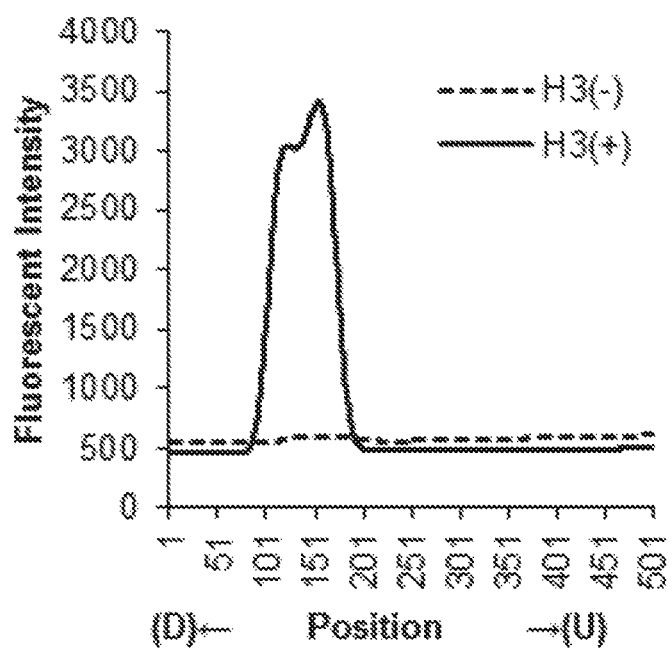
FIG. 5 is a graph illustrating an example of the result obtained by detecting an H3 protein using the second detection method according to the present disclosure in which one type of aptamer probe was used.

FIG. 5 shows the results of the measurements using the fluorescent immunochromato reader, indicating whether or not H3 was detected on the immuno chromatographic test piece. The vertical axis indicates the intensities of fluorescent signals that appeared on the immuno chromatographic test piece, and the horizontal axis indicates the positions on the nitrocellulose membrane on the immuno chromatographic test piece when the right side of the graph is taken as the upstream end. (U) indicates the upstream side, and (D) indicates the downstream side.

As shown in FIG. 5, when the developing solution containing H3 was used, the fluorescent signal was confirmed at the position at which the single-stranded polynucleotide (binding portion) was immobilized, whereas, when the developing solution containing no H3 was used, a fluorescent signal was not detected. It was shown from these results that, in the case where the detection-target substance had a trimeric structure, even when one type of nucleic-acid aptamer probe was used, the detection-target substance H3 could be trapped by using the immuno chromatographic test piece on which a strand (binding portion) complementary to a nucleic-acid aptamer was immobilized and the fluorescent latex particles on which the same sequence (same binding portion) was immobilized.

The disclosure may be embodied in other forms without departing from the spirit or essential characteristics thereof. The embodiments disclosed in this application are to be considered in all respects as illustrative and not limiting. The scope of the disclosure is indicated by the appended claims rather than by the foregoing description, and all changes which come within the meaning and range of equivalency of the claims are intended to be embraced therein.

What is claimed is:

1. A method for detecting a target substance in a sample, comprising:
mixing the sample, a support, a reporter substance, a first trapping substance, and a second trapping substance with one another, each of which are not bound to the others before mixing, to form a reaction mixture, and reacting the reaction mixture such that the sample, the support, the reporter substance, the first trapping substance, and the second trapping substance bind with one another to form at least one of a first complex of "support—first trapping substance—target substance—second trapping substance—reporter substance" or a second complex of "support—second trapping substance—target substance—first trapping substance—reporter substance,"
wherein the support has a first binding portion,
the reporter substance has a second binding portion,
the first trapping substance binds to the target substance and has a first binding partner portion capable of binding to the first binding portion and the second binding portion, and
the second trapping substance binds to the target substance and has a second binding partner portion capable of binding to the first binding portion and the second binding portion; and
detecting a signal from the reporter substance in the first or the second complex, and
wherein in the reacting step, the reaction is capable of forming both the first and second complexes.

2. The method according to claim 1, wherein the first trapping substance and/or the second trapping substance is an aptamer probe.

3. The method according to claim 2, wherein the aptamer probe is a nucleic-acid aptamer.

4. The method according to claim 1, wherein all bonds between the first or second binding partner portion and the first or second binding portion are formed by non-covalent interaction.

5. The method according to claim 4, wherein the bonds formed by non-covalent interaction are bonds between nucleic acids complementary to each other.

6. The method according to claim 1, wherein the first trapping substance and the second trapping substance are the same, and the target substance binds to the first trapping substance and the second trapping substance at different positions of the target substance.

7. The method according to claim 1, wherein the method is conducted by an immuno chromatographic method.

8. The method according to claim 1, wherein the reacting comprises developing the sample, the first trapping substance, the second trapping substance, and the reporter substance on the support.

9. The method according to claim 1, wherein the first trapping substance and the second trapping substance has a target substance recognition portion, which is selected from the group consisting of antibodies, low-molecular weight antibodies, peptides, and aptamers.

10. The method according to claim 1, wherein the reporter substance is selected from the group consisting of enzymes, ferritin, fluorescent light-absorbing silica particles, fluorescent light-absorbing latex particles, semiconductor minute particles and gold colloid particles.

* * * * *